(12) United States Patent
Bowden et al.

(10) Patent No.: US 8,227,619 B2
(45) Date of Patent: Jul. 24, 2012

(54) PROCESS FOR THE PREPARATION OF AMIDES

(75) Inventors: Martin Charles Bowden, Bracknell (GB); David Anthony Jackson, Münchwilen (CH); Alexandre Christian Saint-Dizier, Monthey (CH); George Robert Hodges, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 12/992,781

(22) PCT Filed: May 11, 2009

(86) PCT No.: PCT/EP2009/055651
§ 371 (c)(1),
(2), (4) Date: Feb. 21, 2011

(87) PCT Pub. No.: WO2009/138375
PCT Pub. Date: Nov. 19, 2009

(65) Prior Publication Data
US 2011/0178310 A1 Jul. 21, 2011

(30) Foreign Application Priority Data

May 14, 2008 (GB) .................. 0808766.0
May 14, 2008 (GB) .................. 0808772.8

(51) Int. Cl.
C07D 209/56 (2006.01)
C07D 307/93 (2006.01)
C07D 333/78 (2006.01)
C07D 487/08 (2006.01)

(52) U.S. Cl. .................. 548/365.1; 548/374.1; 546/314; 549/13; 549/29; 549/229; 549/356

(58) Field of Classification Search ............... 548/365.1, 548/374.1
See application file for complete search history.

(56) References Cited

U.S. PATENT DOCUMENTS
3,763,234 A 10/1973 Brill

FOREIGN PATENT DOCUMENTS
WO WO-2004/035589 * 4/2004

OTHER PUBLICATIONS

Arnold K et al: "To Catalyze or not to Catalyze? Insight into Direct Amide Bond Formation from Amines and Carboxylic Acids under Thermal and Catalyzed Conditions" Adv. Synth. Catal., vol. 348, Jan. 1, 2006, pp. 813-820.
Maki T. et al:.: "New boron(III)-catalyzed amide and ester condensation reactions" Tetrahedron, vol. 63, Mar. 31, 2007, pp. 8645-8657.
Tang P.: "Boric acid catalyzed amide formation from carboxylic acids and amines: N-benzyl-4-phenylbutyramide" Organic Synthesis, vol. 81, 2005, p. 262.
Ishihara K. et al: "Antimony-templated macrolactamaization of tetraamino esters, Facile synthesis of macrocyclic spermine alkaloids, (+/−)-Verbaskine, and (+/−)-Verbascenine" J. Am Chem. Soc., vol. 118, No. 6, 1996, pp. 1569-1570.
Ishihara K. et al: "3, 4, 5-Trifluorobenzeneboronic Acid as an Extremely Active Amidation Catalyst" J. Org. Chem., vol. 61, No. 13, 1996, pp. 4196-4197.
Nomura, R. et al: "An organoantimony catalyst for peptide synthesis: preparation and aminolysis of triphenylantimony bis(aminoacylate)s" Applied Organometallic Chemistry vol. 2, 1988, pp. 557-560.
Nomura R. et al: "Aminolysis of triphenylantimony dicarboxylates and its application to catalytic amidation" Chem. Lett., 1986, pp. 1901-1904.
Nomura R. et al: "Facile One-Pot amidation of carboxylic acids by amines catalyzed by triphenylstibine oxide/tetraphosphorus decasulfide (Ph3Sb0/P4S10)" J. Org Chem. vol. 56, No. 12, 1991, pp. 4076-4078. Database Beilstein, Beilstein Institute for Organic Chemistry, Frankfurt-Main, DE; accession No. 1560525, & M Terashima, M Fujioka: Heterocycles, vol. 19, No. 1, 1982, pp. 91-92.
Trapani G et al: Trimethylamine-Borane as useful reagent in the N-Acylation or N-Alkylation of Amines by carboxylic acids: Synthesis, Dec. 1982, pp. 1013-1014.

* cited by examiner

Primary Examiner — Kamal Saeed
Assistant Examiner — Janet L Coppins
(74) Attorney, Agent, or Firm — Kody Jones

(57) ABSTRACT

The invention relates to a process for the preparation of fungicidally active compounds such as tricyclic amine derivatives (I). The process involves coupling of a carboxylic 5 acid e.g. a compound of formula (II) with an aniline, e.g. a compound of formula (III) in the presence of a boronic acid catalystor an antimony catalyst (II)(III)(I) wherein R1, R2, R3, R4, R5, R6, R7, X, Y and Het are defined in the specification.

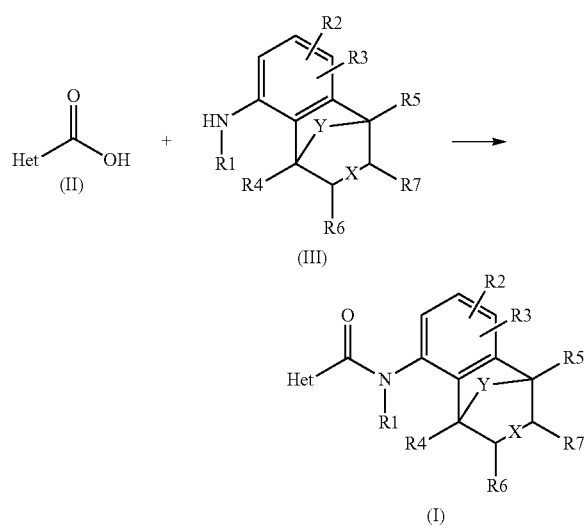

13 Claims, 2 Drawing Sheets

PROCESS FOR THE PREPARATION OF AMIDES

Figure 1:
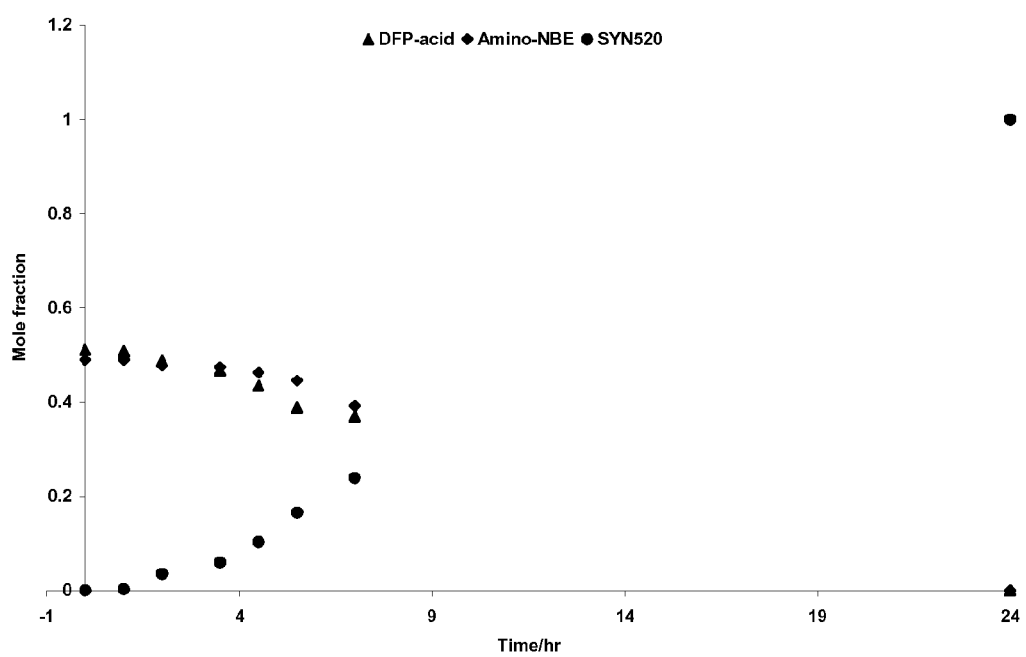

This application is a 371 of International Application No. PCT/EP2009/055651 filed May 11, 2009, which claims priority to GB 0808766.0 filed May 14, 2008, and GB 0808772.8 filed May 14, 2008, the contents of which are incorporated herein by reference.

The present invention relates to a process for the preparation of certain fungicidally active tricyclic amine derivatives and to certain fungicidally active ortho-substituted-cyclopropyl-azolcarboxamides.

Tricyclic amine derivatives having fungicidal activity are disclosed in WO/2004/035589 and WO 2007/048556. Ortho-substituted-cyclopropyl-azolcarboxamides of the formula (IA) are disclosed in WO03/074491

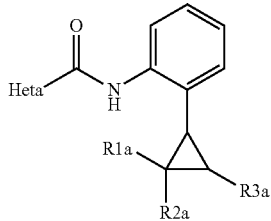

wherein
Heta is a 5-or 6-membered heterocyclic ring containing one to three heteroatoms, each independently selected from oxygen, nitrogen and sulphur, the ring being substituted by groups R4a, R5a and R6a;
R1a is hydrogen or halo;
R2a is hydrogen or halo;
R3a is optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl; and
R4a, R5a and R6a are independently selected from hydrogen, halo, cyano, nitro, $C_{1-4}$ alkyl, $C_{1-4}$ halo alkyl, $C_{1-4}$ alkoxy ($C_{1-4}$) alkyl and $C_{1-4}$ halo alkoxy($C_{1-4}$) alkyl, provided that at least one of R4a, R5a and R6a is not hydrogen.

The compounds disclosed in WO03/074491 have microbiocidal activity, in particular fungicidal activity.

A variety of methods for the preparation of the above compounds have been described in WO2004/035589, WO 2007/048556, and WO 2003/074491.

It has now been surprisingly found that these compounds may be advantageously obtained by coupling the respective amine and carboxylic acid in the presence of a boronic acid catalyst or an antimony catalyst.

The present invention relates to a process for the preparation of compounds of the formula (I)

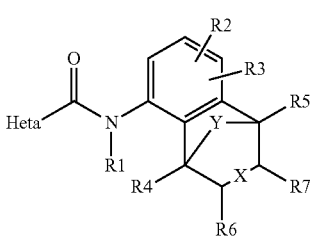

wherein
where Het is a 5- or 6-membered heterocyclic ring containing one to three heteroatoms, each independently selected from oxygen, nitrogen and sulphur, provided that the ring is not 1,2, 3-triazole, the ring being substituted by groups R8, R9 and R10;
X is a single or double bond;
Y is O, S, N(R11), (CR12R13)(CR14R15)m(CR16R17)n or C=C(A)Z in which A and Z are independently $C_{1-6}$ alkyl or halogen;
m is 0 or 1; n is 0 or 1;
R1 is hydrogen, $C_{1-4}$ alkyl, $C_{1-4}$ haloalkyl, $C_{1-4}$ alkoxy, $C_{1-4}$ haloalkoxy, $CH_2C\equiv CR18$, $CH_2CR19=CHR20$, $CH=C=CH_2$ or COR21;
R2 and R3 are each, independently, hydrogen, halogen, $C_{1-4}$ alkyl, $C_{1-4}$ alkoxy or $C_{1-4}$ haloalkoxy;
R4, R5, R6 and R7 are each, independently, hydrogen, halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, hydroxymethyl, $C_{1-4}$ alkoxymethyl, $C(O)CH_3$ or $C(O)OCH_3$;
R8, R9 and R10 are each, independently, hydrogen, halogen, cyano, nitro, $C_{1-4}$ alkyl, $C_{1-4}$ haloalkyl, $C_{1-4}$ alkoxy ($C_14$alkylene or $C_{1-4}$ haloalkoxy($C_14$alkylene, provided that at least one of R8, R9 and R10 is not hydrogen;
R11 is hydrogen, $C_{1-4}$ alkyl, benzyl (in which the phenyl group is optionally substituted with up to three substituents, each independently selected from halogen, $C_{1-4}$ alkyl, $C_{1-4}$ haloalkyl and $C_{1-4}$ alkoxy), formyl, $C(O)C_{1-4}$ alkyl (optionally substituted by halogen or $C_{1-4}$ alkoxy), $C(=O)$ O—$C_{1-6}$ alkyl (optionally substituted by halogen, $C_{1-4}$ alkoxy or cyano) or $C_{1-4}$ alkoxy ($C_{1-4}$ alkylene;
R12, R13, R14, R15, R16 and R17 are each, independently, hydrogen, halogen, hydroxy, $C_{1-6}$ alkyl, $C_{2-6}$ alkenyl [both optionally substituted by halogen, hydroxy, $C_{1-4}$ alkoxy, =O, aryl or O—C(O)—$C_{1-4}$ alkyl or a 3-7 membered carboxylic ring (itself optionally substituted by up to three methyl groups)], a 3-7 membered saturated ring (optionally substituted by up to three methyl groups and optionally containing one heteroatom selected from nitrogen and oxygen) or $C_{1-4}$ alkoxy; or R12 and R13 together with the carbon atom to which they are attached form the group C=O or a 3-5 membered carbocyclic ring (optionally substituted by up to three methyl groups and optionally with up to 2 heteroatoms each independently selected from O and N); or R12 and R13 together form a $C_{1-6}$ alkylidene (optionally substituted by up to three methyl groups) or a $C_{3-6}$ cycloalkylidene group (optionally substituted by up to three methyl groups);
R18, R19 and R20 are each, independently, hydrogen, halogen, $C_{1-4}$ alkyl, $C_{1-4}$ haloalkyl or $C_{1-4}$ alkoxy($C_{1-4}$alkylene; and
R21 is hydrogen, $C_{1-6}$ alkyl, $C_{1-6}$ haloalkyl, $C_{1-4}$ alkoxy ($C_{1-4}$ alkylene, $C_{1-4}$ alkyl-S—($C_{1-4}$) alkylene, $C_{1-4}$ alkoxy or aryl;
comprising the step of reacting a carboxylic acid of formula (II)

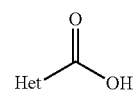

wherein Het is as defined above with an aniline of the formula (III)

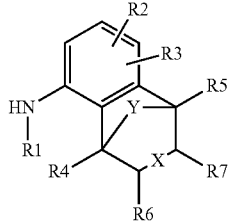

wherein R1, R2, R3, R4, R5, R6, R7, X and Y are as defined above;

in the presence of a boronic acid catalyst or an antimony catalyst.

Halogen is fluoro, chloro, bromo or iodo; preferably fluoro, chloro or bromo.

Each alkyl moiety is a straight or branched chain and is, for example, methyl, ethyl, n-propyl, n-butyl, n-pentyl, n-hexyl, iso-propyl, sec-butyl, iso-butyl, tert-butyl, neo-pentyl, n-heptyl, 1,3-dimethylbutyl, 1,3-dimethylpentyl,1-methyl-3-ethyl-butyl or 1,3,3-trimethylbutyl. Likewise, each alkylene moiety is a straight or branched chain.

Haloalkyl moieties are alkyl moieties which are substituted by one or more of the same or different halogen atoms and are, for example, $CF_3$, $CF_2Cl$, $CHF_2$, $CH_2F$, $CCl_3$, $CF_3CH_2$, $CHF_2CH_2$, $CH_2FCH_2$, $CH_3CHF$ or $CH_3CF_2$.

Alkenyl and alkynyl moieties can be in the form of straight or branched chains.

Each alkenyl moiety, where appropriate, may be of either the (E)- or (Z)-configuration.

A 3-5 membered carbocyclic ring includes a spiro-three or five membered ring.

Aryl includes phenyl, naphthyl, anthracyl, fluorenyl and indanyl but is preferably phenyl.

Alkyliden moieties may be in the form of straight or branched chains. Alkyliden includes methylidene[$CH_2$=], ethylidene [$CH_3C(H)$=], n-propylidene, i-propylidene [$(CH_3)_2C$=], n-butylidene, i-butylidene, 2-butylidene, n-pentylidene, i-pentylidene, neo-pentylidene, 2-pentylidene, n-hexylidene, 2-hexylidene, 3-hexylidene, i-hexylidene and neo-hexylidene.

Cycloalkyl includes cyclopropyl, cyclobutyl, cyclopentyl, cyclohexyl, cycloheptyl and cyclooctyl.

Cycloalkenyl includes cyclobutenyl, cyclopentenyl, cyclohexenyl and cycloheptenyl.

Cycloalkylidene includes cyclopropylidene [$c(C_3H_4)$=], cyclobutylidene, cyclopentylidene and cyclohexylidene.

In one aspect of the invention, R11 is hydrogen, $C_{1-4}$ alkyl, benzyl (in which the phenyl group is optionally substituted with up to three substituents, each independently selected from halogen, $C_{1-4}$ alkyl, $C_{1-4}$ haloalkyl and $C_{1-4}$ alkoxy), formyl, $C(O)C_{1-4}$ alkyl or $C_{1-4}$ alkoxy ($C_{1-4}$) alkylene.

In another aspect of the invention, R12, R13, R14, R15, R16 and R17 are each, independently, hydrogen, $C_{1-4}$ alkyl or $C_{1-4}$ alkoxy.

Het is preferably pyrrolyl, pyrazolyl, thiazolyl, oxazolyl, pyridinyl, pyrimidyl, pyridazinyl, 2,3-hydro-[1,4]oxathiine-6-yl, oxazinyl, thiazinyl or triazinyl.

Het is more preferably pyrrolyl, pyrazolyl, thiazolyl, oxazolyl, pyridinyl or 2,3-dihydro-[1,4] oxathiine-yl.

Het is even more preferably pyrrolyl, pyrazolyl, thiazolyl or pyridinyl.

Het is most preferably pyrrolyl or pyrazolyl.

Preferably X is a single bond.

In one aspect, Y is O, S, N(R11), $CH_2$, $CH_2CH_2$, $CH_2CH_2CH_2$, $C(CH_3)_2$, $CH(CH_3)$, CH $C_2H_5$), $C(CH_3)$ ($C_2H_5$), $CH(OCH_3)$ or $C(OCH_3)_2$; more preferably N(R11), O, S, $CH_2$, $CH_2CH_2$, $CH_2CH_2CH_2$, $C(CH_3)_2$, $CH(CH_3)$ or $CH(C_2H_5)$; even more preferably N(R11), O, S, $CH_2$ or $CH_2CH_2$; and still more preferably O, $CH_2$ or N (R11). Preferably Y is O, N(R11) or (CR12R13)(CR14R15)m (CR16R17)n. More preferably Y is O or (CR12R13) (CR14R15)m(CR16R17)n. Even more preferably Y is (CR12R13)(CR14R15)m(CR16R17)n. Still more preferably Y is (CR12R13), e.g. $CHCH(CH_3)CH_3$.

In a further aspect, Y is C=C(A)Z in which A and Z are independently $C_{1-6}$ alkyl or halogen. Preferably A and Z are independently halogen, more preferably both A and Z are chlorine.

Preferably n is 0.
Preferably m is 0.
Preferably R1 is hydrogen, $CH_2C$≡CR18, CH=C=$CH_2$ or COR21.

More preferably R1 is hydrogen, $CH_2C$≡CH, CH=C=$CH_2$, C(O)H or $C(O)CH_3$.

Yet more preferably R1 is hydrogen, $CH_2C$≡CH, CH=C=$CH_2$ or $C(O)CH_3$.

Even more preferably R1 is hydrogen, $CH_2C$≡CH or CH=C=$CH_2$.

Most preferably R1 is hydrogen.
Preferably R2 is hydrogen, halogen or $C_{1-4}$ alkyl.
More preferably R2 is hydrogen or halogen.
Most preferably R2 is hydrogen.
Preferably R3 is hydrogen or methyl.
More preferably R3 is hydrogen.
Preferably R4 is hydrogen, $C_{1-4}$ alkyl, halogen, $C_{1-4}$ haloalkyl, $C_{1-4}$ alkoxy, $C(O)CH_3$ or $C(O)OCH_3$.

More preferably R4 is hydrogen, $C_{1-2}$ alkyl, halogen, $CF_3$, methoxy, $C(O)CH_3$ or $C(O)OCH_3$.

Even more preferably R4 is hydrogen, methyl, chlorine, $CF_3$ or methoxy.

Most preferably R4 is hydrogen or methyl.
Preferably R5 is hydrogen, $C_{1-4}$ alkyl, halogen, $C_{1-4}$ haloalkyl, $C_{1-4}$ alkoxy, $C(O)CH_3$ or $C(O)OCH_3$.

More preferably R5 is hydrogen, $C_{1-2}$ alkyl, chlorine, $CF_3$, methoxy, $C(O)CH_3$ or $C(O)OCH_3$.

Most preferably R5 is hydrogen or methyl.
Preferably R6 is hydrogen, $C_{1-4}$ alkyl, $C_{1-4}$ alkoxy or $C(O)CH_3$.

More preferably R6 is hydrogen, methyl, methoxy or $C(O)CH_3$.

Most preferably R6 is hydrogen or methyl.
Preferably R7 is hydrogen, $C_{1-4}$ alkyl, $C_{1-4}$ alkoxy or $C(O)CH_3$.

More preferably R7 is hydrogen, methyl, methoxy or $C(O)CH_3$.

Most preferably R7 is hydrogen or methyl.
Preferably R8 is hydrogen, halogen, $C_{1-4}$ alkyl, $C_{1-4}$ haloalkyl or methoxymethylene.

More preferably R8 is hydrogen, chloro, fluoro, bromo, $C_{1-2}$ alkyl, $CF_3$, $CF_2Cl$, $CHF_2$, $CH_2F$ or methoxymethylene.

Even more preferably R8 is hydrogen, chloro, fluoro, $C_{1-2}$ alkyl, $CF_3$, $CF_2Cl$, $CHF_2$, $CH_2F$ or methoxymethylene.

Most preferably R8 is hydrogen, chloro, fluoro, methyl, $CF_3$, $CHF_2$ or $CH_2F$.

Preferably R9 is hydrogen, halogen, $C_{1-4}$ alkyl or $C_{1-4}$ haloalkyl or methoxymethylene.

More preferably R9 is hydrogen, chloro, fluoro, bromo, $C_{1-2}$ alkyl, $CF_3$, $CF_2Cl$, $CHF_2$, $CH_2F$ or methoxymethylene.

Even more preferably R9 is hydrogen, chloro, fluoro, $C_{1-2}$ alkyl, $CF_3$, $CF_2Cl$, $CHF_2$, $CH_2F$ or methoxymethylene.

Most preferably R9 is hydrogen, chloro, fluoro, methyl, $CF_3$, $CHF_2$ or $CH_2F$.

Preferably R10 is hydrogen, halogen, $C_{1-4}$ alkyl, $C_{1-4}$ haloalkyl or methoxymethylene.

More preferably R10 is hydrogen, chloro, fluoro, bromo, $C_{1-2}$ alkyl, $CF_3$, $CF_2Cl$, $CHF_2$, $CH_2F$ or methoxymethylene.

Even more preferably R10 is hydrogen, chloro, fluoro, $C_{1-2}$ alkyl, $CF_3$, $CF_2Cl$, $CHF_2$, $CH_2F$ or methoxymethylene.

Most preferably R10 is hydrogen, chloro, fluoro, methyl, $CF_3$, $CHF_2$ or $CH_2F$.

In one aspect of the invention R11 is hydrogen, $C_{1-4}$ alkyl, benzyl, formyl, $C(O)CH_3$ or $C(O)OC(CH_3)_3$; more preferably hydrogen or $C_{1-2}$ alkyl.

Preferably R11 is $C_{1-4}$ alkyl, formyl, $C(O)CH_3$ or $C(O)OC_{1-6}$ alkyl (optionally substituted by halogen, CN or $C_{1-4}$ alkoxy).

More preferably R11 is $C(O)OC_{1-4}$ alkyl.

In one aspect of the invention R12, R13, R14, R15, R16 and R17 are each, independently, hydrogen, $C_{1-2}$ alkyl or methoxy.

Preferably R12 and R13 are each, independently, hydrogen, halogen, $C_{1-5}$ alkyl, $C_{1-3}$ alkoxy, $CH_2OH$, $CH(O)$, $C_{3-6}$ cycloalkyl, $CH_2O$—$C(=O)CH_3$, $CH_2$—$C_{3-6}$ cycloalkyl or benzyl; or R12 and R13 together with the carbon atom to which they are attached form the group C=O or a 3-5 membered carbocyclic ring; or R12 and R13 together form $C_{1-5}$ alkylidene or $C_{3-6}$ cycloalkylidene.

More preferably R12 and R13 are, independently, H, $CH_3$, $C_2H_5$, n-$C_3H_7$, i-$C_3H_7$, n-$C_4H_9$, sec-$C_4H_9$, i-$C_4H_9$, $CH(C_2H_5)_2$, $CH_2$-cyclopropyl or cyclopentyl; or R12 and R13 together with the carbon atom to which they are attached form a 3-membered or 5-membered carbocyclic ring.

Preferably R14 is H or $CH_3$.
Preferably R15 is H or $CH_3$.
Preferably R16 is H or $CH_3$.
Preferably R17 is H or CH3.
Preferably R18 is hydrogen, chloro, bromo, methyl or methoxy.

More preferably R18 is hydrogen, chloro or methyl.
Most preferably R18 is hydrogen.
Preferably R19 is hydrogen, chloro, bromo, methyl or methoxy.

More preferably R19 is hydrogen, chloro or methyl.
Most preferably R19 is hydrogen.
Preferably R20 is hydrogen, chloro, bromo, methyl or methoxy.

More preferably R20 is hydrogen, chloro or methyl.
Most preferably R20 is hydrogen.
Preferably R21 is hydrogen, methyl, $OC(CH_3)_3$ or $CH_3OCH_2$.

For example,
Het is pyrrolyl or pyrazolyl, either being substituted by groups R8, R9 and R10;
X is a single bond;
Y is $(CR12R13)(CR14R15)_m(CR16R17)_n$ or C=C(A)Z in which A and Z are independently $C_{1-6}$ alkyl or halogen;
m is 0 or 1;
n is 0 or 1;
R1 is hydrogen;
R2 and R3 are each, independently, hydrogen, halogen, $C_{1-4}$ alkyl, $C_{1-4}$ alkoxy or $C_{1-4}$ haloalkoxy;
R4, R5, R6 and R7 are each, independently, hydrogen, halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, hydroxymethyl, $C_{1-4}$ alkoxymethyl, $C(O)CH_3$ or $C(O)OCH_3$;
R8, R9 and R10 are each, independently, hydrogen, halogen, cyano, nitro, $C_{1-4}$ alkyl, $C_{1-4}$ haloalkyl, $C_{1-4}$ alkoxy($C_{1-4}$)alkylene or $C_{1-4}$ haloalkoxy($C_{1-4}$alkylene, provided that at least one of R8, R9 and R10 is not hydrogen;
R12 and R13 are each, independently, hydrogen, halogen, $C_{1-5}$ alkyl, $C_{1-3}$ alkoxy, $CH_2OH$, $CH(O)$, $C_{3-6}$ cycloalkyl, $CH_2O$—$C(=O)CH_3$, $CH_2$—$C_{3-6}$ cycloalkyl or benzyl;
or R12 and R13 together with the carbon atom to which they are attached form the group C=O or a 3-5 membered carbocyclic ring;
or R12 and R13 together form $C_{1-5}$ alkylidene or $C_{3-6}$ cycloalkylidene; and
R14, R15, R16 and R17 are each, independently, H or $CH_3$.

Preferably, R8, R9 and R10 are each, independently, hydrogen, chloro, fluoro, methyl, $CF_3$, $CHF_2$ or $CH_2F$, provided that at least one of R8, R9 and R10 is not hydrogen. Preferably, n is 0 and m is 0. Preferably, R12 and R13 are each, independently, hydrogen, $C_{1-4}$ alkyl or $C_{1-4}$ alkoxy. Preferably, R2 is hydrogen, halogen or $C_{1-4}$ alkyl. Preferably, R3 is hydrogen or methyl. Preferably Het is pyrazolyl.

Preferably Het is a group of formula (VIIA)

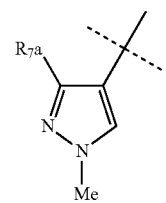

(VIIA)

in which R7a is selected from $CF_3$ and $CHF_2$;
Preferably, R1, R2, R3, R4, R5, R6, R7 are each independently hydrogen.

Preferably, X is a single bond;
Preferably, Y is $C=CCl_2$ or $CHCH(CH_3)CH_3$.

For example, in one embodiment:
Het is a group of formula (VIIA)

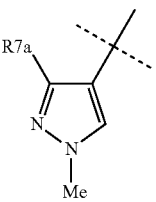

(VIIA)

in which R7a is selected from $CF_3$ and $CHF_2$;
R1, R2, R3, R4, R5, R6, R7 are each independently hydrogen;
X is a single bond;
Y is $CHCH(CH_3)CH_3$;
and the catalyst is a boronic acid catalyst or an antimony catalyst, e.g. boric acid or an aryl boronic acid such as 3,5-bis-(trifluoromethyl)-phenylboronic acid or 2-(N,N-dimethylaminomethyl)phenylboronic acid, or an antimony III alkoxide such as $Sb(OEt)_3$. For example, the catalyst may be 3,5-bis-(trifluoromethyl)-phenylboronic acid or $Sb(OEt)_3$.

For example, in further embodiment:
Het is a group of formula (VIIA)

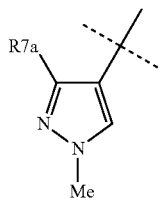
(VIIA)

in which R7a is selected from $CF_3$ and $CHF_2$;
R1, R2, R3, R4, R5, R6, R7 are each independently hydrogen;
X is a single bond;
Y is C=C(A)Z in which A and Z are, independently fluoro, chloro or bromo, preferably chloro;
and the catalyst is a boronic acid catalyst or an antimony catalyst, e.g. boric acid or an aryl boronic acid such as 3,5-bis-(trifluoromethyl)-phenylboronic acid or 2-(N,N-dimethylaminomethyl)phenylboronic acid, or an antimony III alkoxide such as $Sb(OEt)_3$. For example, the catalyst may be boric acid or 2-(N,N-dimethylaminomethyl)phenylboronic acid.

According to a very highly preferred embodiment, the invention relates to a process for the preparation of a compound of formula (VI)

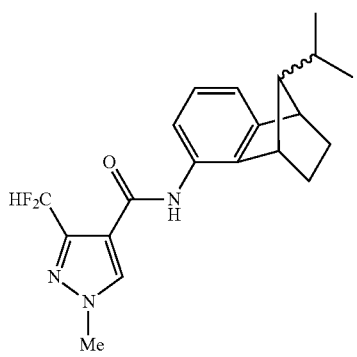
(VI)

comprising reacting a carboxylic acid of formula (IV)

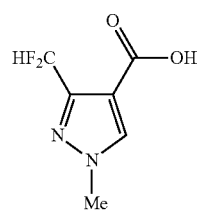
(IV)

with an aniline of formula (V)

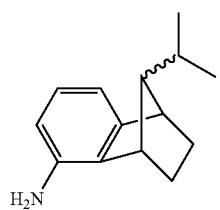
(V)

in the presence of a boronic acid catalyst or an antimony catalyst, e.g. boric acid or an aryl boronic acid such as 3,5-bis-(trifluoromethyl)-phenylboronic acid or 2-(N,N-dimethylaminomethyl)phenylboronic acid, or an antimony III alkoxide such as $Sb(OEt)_3$. For example, the catalyst may be 3,5-bis-(trifluoromethyl)-phenylboronic acid or $Sb(OEt)_3$.

According to a further highly preferred embodiment of the invention, the invention relates to a process for the preparation of a compound of formula (VIII)

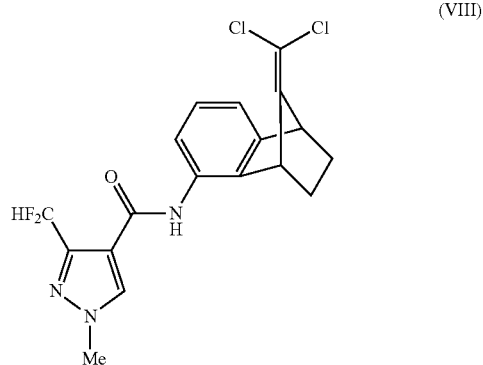
(VIII)

comprising reacting a carboxylic acid of formula (IV)

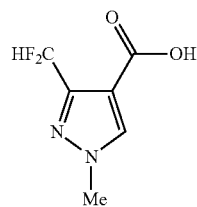
(IV)

with an aniline of formula (VII)

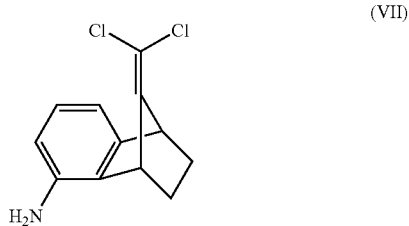
(VII)

in the presence of a boronic acid catalyst or an antimony catalyst, e.g. boric acid or an aryl boronic acid such as 3,5-bis-(trifluoromethyl)-phenylboronic acid or 2-(N,N-dimethylaminomethyl)phenylboronic acid, or an antimony III alkoxide such as $Sb(OEt)_3$. For example, the catalyst may be boric acid or 2-(N,N-dimethylaminomethyl)phenylboronic acid.

In a further embodiment, the present invention provides a process for the preparation of compounds of formula (IA)

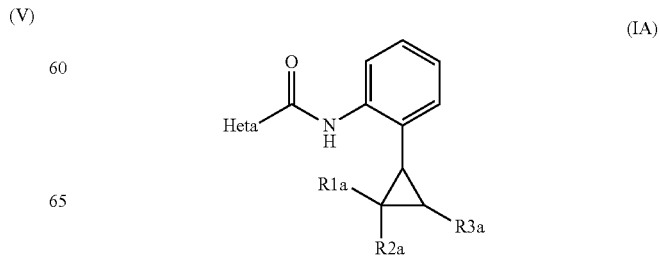
(IA)

wherein

Heta is a 5-or 6-membered heterocyclic ring containing one to three heteroatoms, each independently selected from oxygen, nitrogen and sulphur, the ring being substituted by groups R4a, R5a and R6a;

R1a is hydrogen or halogen;

R2a is hydrogen or halogen;

R3a is optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl; and R4a, R5a and R6a are independently selected from hydrogen, halogen, cyano, nitro, $C_{1-4}$ alkyl, $C_{1-4}$ haloalkyl, $C_{1-4}$ alkoxy($C_{1-4}$) alkyl and $C_{1-4}$ haloalkoxy($C_{1-4}$) alkyl, provided that at least one of R4a, R5a and R6a is not hydrogen comprising reacting a carboxylic acid of formula (IIA)

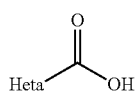

(IIA)

with an aniline of the formula (IIIA)

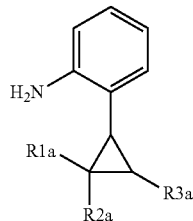

(IIIA)

in the presence of a boronic acid catalyst or an antimony catalyst.

Halogen is fluoro, chloro or bromo.

Each alkyl moiety is a straight or branched chain and is, for example, methyl, ethyl, n-propyl, n-butyl, n-pentyl, n-hexyl, iso-propyl, n-butyl, sec-butyl, iso-butyl, tert-butyl or neopentyl.

When present, each optional substituent on an alkyl moiety is, independently, selected from halogen, hydroxy, cyano, $C_{1-4}$ alkoxyC(=O), formyl, nitro, $C_{1-4}$ alkoxy, $C_{1-4}$ haloalkoxy, $C_{1-4}$ alkylthio, $C_{1-4}$ haloalkylthio, HC(OR')=N and R'R''NN=C(H); where R' and R'' are, independently, hydrogen or $C_{1-4}$ alkyl.

Alkenyl and alkynyl moieties can be in the form of straight or branched chains.

The alkenyl moieties, where appropriate, can be of either the (E)- or (Z)-configuration. Examples are vinyl, allyl and propargyl.

When present, each optional substituent on alkenyl or on alkynyl is, independently, selected from those optional substituents given above for an alkyl moiety.

Cycloalkyl includes cyclopropyl, cyclobutyl, cyclopentyl and cyclohexyl.

When present, each optional substituent on cycloalkyl is, independently, selected from $C_{1-3}$ alkyl and those optional substituents given above for an alkyl moiety.

The term heterocyclyl refers to a non-aromatic or aromatic ring containing up to 10 atoms including one or more (preferably one or two) heteroatoms selected, each independently, from O, S and N. Examples of such rings include 1,3-dioxolanyl, tetrahydrofuranyl, morpholinyl, thienyl and furyl.

When present, each optional substituent on phenyl or on heterocyclyl is, independently, selected from $C_{1-6}$ alkyl and those optional substituents given above for an alkyl moiety. When present, there are up to four optional substituents on phenyl, each independently selected.

When present, each optional substituent on an alkyl moiety is, independently, selected from the preferred list of halo, hydroxy, methoxy, trifluoromethoxy, difluoromethoxy, cyano and nitro.

When present, each optional substituent on alkenyl or on alkynyl is, independently, selected from the preferred list of halogen and cyano.

When present, each optional substituent on cycloalkyl is, independently, selected from the preferred list of methyl, ethyl, trifluoromethyl, methoxy, trifluoromethoxy and cyano.

When present, each optional substituent on phenyl or on a heterocyclyl group is, independently, selected from the preferred list of halo, hydroxy, methoxy, trifluoromethoxy, difluoromethoxy and cyano.

It is preferred that Heta is pyrrolyl, pyrazolyl, thiazolyl, pyridinyl, pyrimidinyl, thiophenyl, furyl, isothiazolyl or isoxazolyl (more preferably pyrrolyl, pyrazolyl or thiazolyl), each being substituted by groups R4a, R5a and R6a.

Preferably

Heta is pyrrolyl, pyrazolyl or thiazolyl, each being substituted by groups R4a, R5a, R6a;

R1a is hydrogen, fluoro, chloro or bromo;

R2a is hydrogen, fluoro, chloro or bromo;

R3a is optionally substituted $C_{2-12}$ alkyl, wherein, when present, each optional substituent is, independently, selected from fluoro, chloro, bromo, hydroxy, cyano, $C_{1-4}$ alkoxyC(=O), formyl, nitro, $C_{1-4}$ alkoxy, $C_{1-4}$ haloalkoxy, $C_{1-4}$ alkylthio, $C_{1-4}$ haloalkylthio, HC(OR')=N and R'R''NN=C(H); optionally substituted $C_{2-12}$ alkenyl, wherein, when present, each optional substituent is, independently, selected from fluoro, chloro, bromo, hydroxy, cyano, $C_{1-4}$ alkoxyC(=O), formyl, nitro, $C_{1-4}$-alkoxy, $C_{1-4}$ haloalkoxy, $C_{1-4}$ alkylthio, $C_{1-4}$ haloalkylthio, HC(OR')= N and R'R''NN=C(H); optionally substituted $C_{2-12}$ alkynyl, wherein, when present, each optional substituent is, independently, selected from fluoro, chloro, bromo, hydroxy, cyano, $C_{1-4}$ alkoxyC(=O), formyl, nitro, $C_{1-4}$ alkoxy, $C_{1-4}$ haloalkoxy, $C_{1-4}$ alkylthio, $C_{1-4}$ haloalkylthio, HC(OR=)=N and R'R''NN=C(H); optionally substituted $C_{3-12}$ cycloalkyl, wherein, when present, each optional substituent is, independently, selected from $C_{1-3}$ alkyl, fluoro, chloro, bromo, hydroxy, cyano, $C_{1-4}$ alkoxyC(=O), formyl, nitro, $C_{1-4}$ alkoxy, $C_{1-4}$ haloalkoxy, $C_{1-4}$ alkylthio, $C_{1-4}$ haloalkylthio, HC(OR')=N and R'R''NN=C(H); optionally substituted phenyl, wherein, when present, each optional substituent is, independently, selected from $C_{1-6}$ alkyl, fluoro, chloro, bromo, hydroxy, cyano, $C_{1-4}$ alkoxyC(=O), formyl, nitro, $C_{1-4}$ alkoxy, $C_{1-4}$ haloalkoxy, $C_{1-4}$ alkylthio, $C_{1-4}$ haloalkylthio, HC(OR')= N and R'R''NN=C(H); or optionally substituted heterocyclyl, wherein, when present, each optional substituent is, independently, selected from $C_{1-6}$ alkyl, fluoro, chloro, bromo, hydroxy, cyano, $C_{1-4}$ alkoxyC(=O), formyl, nitro, $C_{1-4}$ alkoxy, $C_{1-4}$ haloalkoxy, $C_{1-4}$ alkylthio, $C_{1-4}$ haloalkylthio, HC(OR')=N; R' and R'' are, independently, hydrogen or $C_{1-4}$ alkyl; and R4a, R5a, and R6a are, independently, selected from hydrogen, fluoro, chloro, bromo, cyano, nitro, $C_{1-4}$ alkyl, $C_{1-4}$ haloalkyl, $C_{1-4}$ alkoxy($C_{1-4}$)alkyl and $C_{1-4}$ haloalkoxy ($C_14$alkyl, provided that at least one of R4a, R5a, and R6a is not hydrogen.

Preferably R1a and R2a are, independently, hydrogen or fluoro.

Preferably R3a is $C_{2-6}$ alkyl, optionally substituted $C_{3-8}$ cycloalkyl, phenyl, thienyl or furyl.

Preferably R4a, R5a and R6a are, independently, selected from hydrogen, halogen, C1-4 alkyl, $C_{1-4}$ haloalkyl and $C_{1-4}$ alkoxy($C_{1-4}$)alkyl; provided that at least one of R4a, R5a and R6a is not hydrogen. More preferably R4a, R5a, and R6a are, independently, selected from hydrogen, halogen, methyl, $C_{1-2}$ haloalkyl and methoxymethyl; provided that at least one of R4a, R5a and R6a is not hydrogen.

Preferably, Heta is pyrazolyl. More preferably, Heta is pyrazol-4-yl. More preferably, Heta is a group of formula (VIIA)

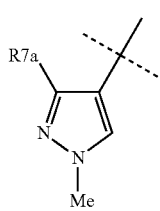

(VIIA)

wherein R7a is selected from $CF_3$ and $CHF_2$. Preferably, R7a is $CHF_2$.

Preferably, R1a is hydrogen. Preferably, R2a is hydrogen. More preferably, R1a and R2a are hydrogen.

Preferably, R3a is optionally substituted cycloalkyl. More preferably, R3a is optionally substituted cyclopropyl. More preferably, R3a is a group of the formula (VIIIA)

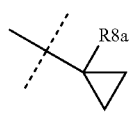

(VIIIA)

wherein R8a is H or $C_{1-6}$ alkyl. Preferably, R8a is H or Methyl. More preferably, R8a is H.

For example,

Heta is a group of formula (VIIA)

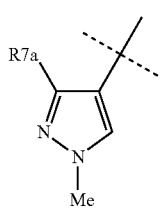

(VIIA)

wherein R7a is selected from $CF_3$ and $CHF_2$;

R1a is R2a, and R3a are hydrogen;
R3a is a group of the formula (VIIIA)

(VIIIA)

wherein R8a is H or C1-4 alkyl, preferably H or Methyl, more preferably H; and the catalyst is a boronic acid catalyst or an antimony catalyst, e.g. boric acid or an aryl boronic acid such as 3,5-bis-(trifluoromethyl)-phenylboronic acid or 2-(N,N-dimethylaminomethyl)phenylboronic acid, or an antimony III alkoxide such as $Sb(OEt)_3$. For example, the catalyst may be boric acid or 2-(N,N-dimethylaminomethyl)phenylboronic acid.

According to a very highly preferred embodiment, the invention relates to a process for the preparation of a compound of formula (IXA)

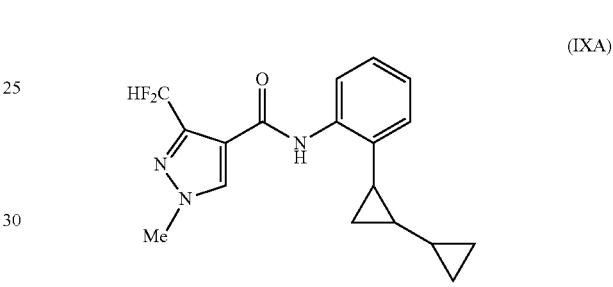

(IXA)

comprising reacting an acid of formula (XA)

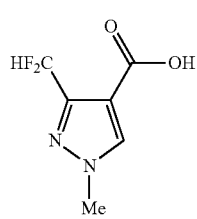

(XA)

with an aniline of formula (XIA)

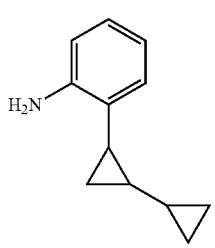

(XIA)

in the presence of a boronic acid catalyst or an antimony catalyst, e.g. boric acid or an aryl boronic acid such as 3,5-bis-(trifluoromethyl)-phenylboronic acid or 2-(N,N-dimethylaminomethyl)phenylboronic acid, or an antimony III alkoxide such as $Sb(OEt)_3$. For example, the catalyst may be boric acid or 2-(N,N-dimethylaminomethyl)phenylboronic acid.

Ratio of Reagents

Preferably, the molar ratio of acid (II) or (IIA):aniline (III) or (IIIA) is in the range of from 10:1 to 1:10. More preferably, the molar ratio of acid (II) or (IIA):aniline (III) or (IIIA) is in the range of from 5:1 to 1:5. More preferably, the molar ratio of acid (II) or (IIA):aniline (III) or (IIIA) is in the range of from 2:1 to 1:2. More preferably, the molar ratio of acid (II) or (IIA):aniline (III) or (IIIA) is in the range of from 1.2:1 to 1:1.2. More preferably, the molar ratio of acid (II) or (IIA):aniline (III) or (IIIA) is in the range of from 1.1:1 to 1:1.1.

Solvent

The reaction of the invention is optionally (and preferably) conducted in a suitable solvent. Suitable solvents include, but are not limited to, linear, branched or cyclic aliphatic hydrocarbons, such as ligroin or cyclohexane, pentane, hexane, heptane, octane, as well as aromatic solvents, such as benzene, toluene, xylene, monochlorobenzene, dichlorobenzene, trichlorobenzene.

A preferred solvent is xylene.

Temperature

The reaction of the invention may be carried out at a temperature such that an acceptable rate of reaction is attained. Preferably, the reaction is conducted at a temperature of from 0° C. to 200° C. More preferably, the reaction is conducted at a temperature of from 50° C. to 180° C. More preferably, the reaction is conducted at a temperature of from 100° C. to 170° C. More preferably, the reaction is conducted at a temperature of from 130° C. to 150° C.

Removal of Water

Preferably, provision is made for removal of water from the reaction mixture, e.g. removal of water prior to completion of the reaction. Water may be removed from the reaction continuously. A suitable method is azeotropic removal of water. Suitable apparatus for conducting azeotropic removal of water will be known to those skilled in the art. We have found that removal of water is highly desirable in order to achieve a commercially useful conversion to product.

Boronic Acid

Examples of the boronic acids include boric acid, phenylboronic acid, 2-methylphenylboronic acid, 3-methylphenylboronic acid, 4-methylphenylboronic acid, 2,3-dimethylphenylboronic acid, 4-dimethylphenylboronic acid, 2,5-dimethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluorophenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 4,5-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-dimethylaminomethyl)phenylboronic acid, furan-2-boronic acid, furan-3-boronic acid, 4-formyl-2-furanboronic acid, dibenzofuran-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 5-methylthiophene-2-boronic acid, 2-acetylthiophene-5-boronic acid, 5-methylthiophene-2-boronic acid, benzothiophene-2-boronic acid, dibenzothiophene-4-boronic acid, pyridine-3-boronic acid, pyridine-4-boronic acid, pyrimidine-5-boronic acid, quinoline-8-boronic acid, isoquinoline-4-boronic acid, 4-benzenebis(boronic acid), phenylboronic acid-pinacol ester, and 4-cyanophenylboronic acid-pinacol ester.

A preferred class of boronic acids are aryl boronic acids. Most preferred is 2-(N,N-dimethylaminomethyl)phenylboronic acid and 3,5-trifluoromethylphenylboronic acid.

An alternative preferred boronic acid is boric acid.

Antimony

Antimony for use as a catalyst in the present invention may be, for example, antimony III or antimony V.

Examples of antimony for use as a catalyst include antimony complexes, e.g. organo antimony complexes such as aryl antimony complexes and saturated and unsaturated carbon chain antimony complexes, with the ligand complexed to the antimony with a suitable coordination atom, e.g. selected from O, S or N. Example of suitable antimony catalysts include:

antimony halides, e.g. $SbCl_3$, antimony oxides, e.g. $Sb_2O_3$, antimony alkoxides, e.g. $Sb(ORx)_3$ in which Rx is alkyl, alkenyl, alkynyl, e.g. C1-C4 alkyl, C2-C4 alkenyl, e.g. C3-C4 alkynyl, in particular $Sb(OEt)_3$, antimony carboxylic acids, e.g. $Sb(O_2CRx)_3$ in which Rx is as defined above, in particular $Sb(Ac)_3$.

Examples of antimony V catalysts include aryl antimony complexes, such as those mentioned in Nomura et al., Chemistry Letters, The Chemical Society of Japan, 1986, pages 1901-1904. These include antimony complexed with aryl groups and carboxylates, e.g. $Ph_3Sb(O_2CRx)_2$ in which Rx is as defined above, particularly $Ph_3Sb(OAc)_2$, and antimony oxides complexed with aryl groups, e.g. $Ph_3SbO$.

Catalyst Recycle

Preferably the catalyst is recycled, e.g. by extracting the catalyst from the reaction solution into the aqueous phase. Extraction of the catalyst may be achieved by changing the pH of the reaction solution, e.g. to alkaline pH, so that the catalyst transfers from the organic phase to the aqueous phase. The catalyst may subsequently be transferred from the aqueous phase to fresh reactant solution by changing the pH, e.g. to acidic pH.

Boronic acid catalysts, such as 3,5-bis-(trifluoromethyl)-phenylboronic acid, are particularly suitable for catalyst recycle by extracting the catalyst from the reactant solution to aqueous phase.

Amount of Catalyst

Preferably, the amount of catalyst employed is up to 50 mol % based on the amount of carboxylic acid (II) or (IIA). More preferably, the amount of catalyst employed is up to 25 mol % based on the amount of carboxylic acid (II) or (IIA). More preferably, the amount of catalyst employed is up to 15 mol % based on the amount of carboxylic acid (II) or (IIA).

Preferably, the amount of catalyst employed is at least 0.01 mol % based on the amount of carboxylic acid (II) or (IIA). More preferably, the amount of catalyst employed is at least 0.1 mol % based on the amount of carboxylic acid (II) or (IIA). More preferably, the amount of catalyst employed is at least 1 mol % based on the amount of carboxylic acid (II) or (IIA).

Preferably, the amount of catalyst employed is between 0.01 and 50 mol % based on the amount of carboxylic acid (II) or (IIA). More preferably, the amount of catalyst employed is between 0.1 and 25 mol % based on the amount of carboxylic acid (II) or (IIA). More preferably, the amount of catalyst employed is between 1 and 15 mol % based on the amount of carboxylic acid (II) or (IIA). More preferably, the amount of catalyst employed is between 8 and 12 mol % based on the amount of carboxylic acid (II) or (IIA).

Preferably, the amount of catalyst employed is up to 50 mol % based on the amount of aniline (III) or (IIIA). More preferably, the amount of catalyst employed is up to 25 mol % based on the amount of aniline (III) or (IIIA). More preferably, the amount of catalyst employed is up to 15 mol % based on the amount of aniline (III) or (IIIA).

Preferably, the amount of catalyst employed is at least 0.01 mol % based on the amount of aniline (III) or (IIIA). More preferably, the amount of catalyst employed is at least 0.1 mol % based on the amount of aniline (III) or (IIIA). More preferably, the amount of catalyst employed is at least 1 mol % based on the amount of aniline (III) or (IIIA).

Preferably, the amount of catalyst employed is between 0.01 and 50 mol % based on the amount of aniline (III) or (IIIA). More preferably, the amount of catalyst employed is between 0.1 and 25 mol % based on the amount of aniline (III) or (IIIA). More preferably, the amount of catalyst employed is between 1 and 15 mol % based on the amount of aniline (III) or (IIIA). More preferably, the amount of catalyst employed is between 8 and 12 mol % based on the amount of aniline (III) or (IIIA).

Usually one type of catalyst will be used in a reaction. However, the invention also covers reactions in which more than one type of catalyst is used, e.g. either separately, sequentially or simultaneously. For example, more than one type of boronic catalyst or antimony catalyst may be used or a boronic acid catalyst and an antimony catalyst may be used.

Synthesis of Starting Materials

Suitable methods for the preparation of carboxylic acids (II) and anilines (III) are disclosed in WO04/035589 and WO 2007/048556. Suitable methods for the preparation of carboxylic acids (IIA) and anilines (IIIA) are disclosed in WO03/074491. Other methods will be apparent to those skilled in the art.

Workup and Isolation of Products

Workup of the reaction mixture is achieved according to well known procedures of synthetic organic chemistry. For example, an aqueous workup may be achieved by the addition of water (or other aqueous solution), and extraction of the desired product with a suitable organic solvent.

Alternatively, the product may be isolated by removing any solvent present by distillation, e.g. under reduced pressure.

Purification of the product may be achieved by any one of a number of methods, e.g. distillation, recrystallization and chromatography.

The present invention will now be described by way of the following non-limiting examples. Those skilled in the art will promptly recognize appropriate variations from the procedures both as to reactants and as to reaction conditions and techniques.

All references mentioned herein are incorporated by reference in their entirety. All aspects and preferred features of the invention may be combined with each other, except where this is evidently not possible.

FIG. 1

FIG. 1 shows the reaction profile of the boronic acid catalysed reaction of Example 2:

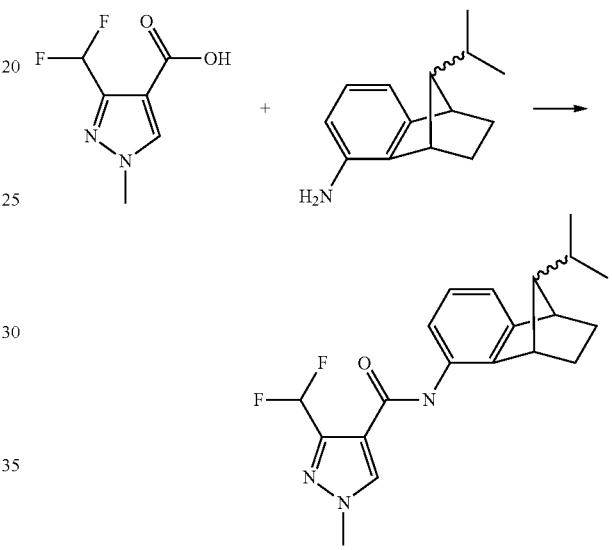

using 10 mole % catalyst, under azeotropic reflux in toluene. The X axis indicates time in hours and the Y axis indicates mole fraction. Triangles represent the acid reactant, diamonds represent the aniline reactant, circles represent product.

FIG. 2

Figure 2:
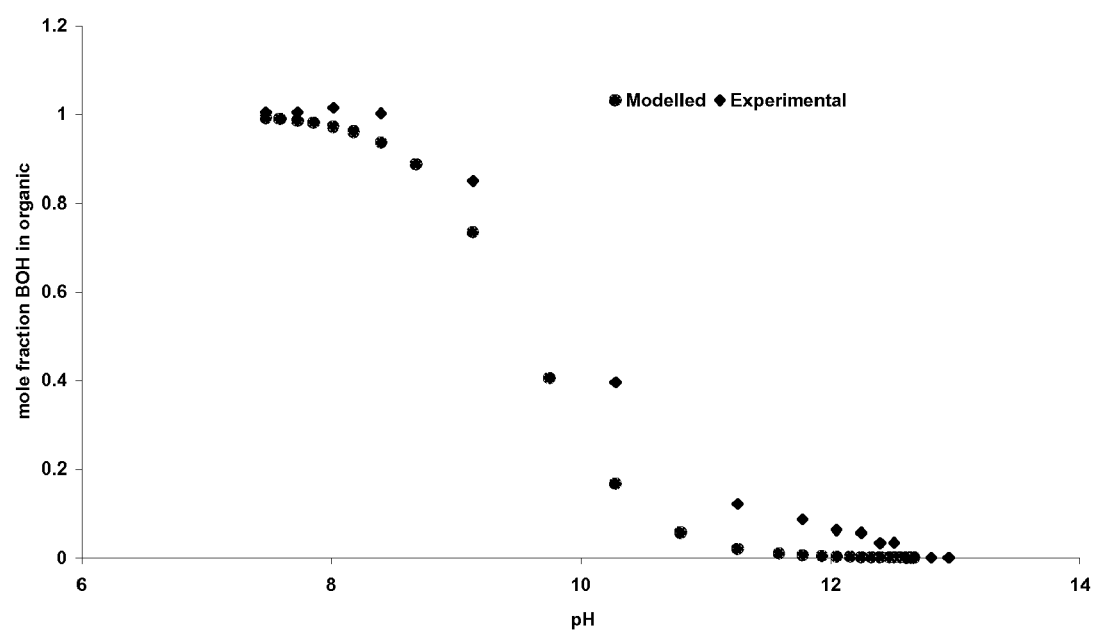

FIG. 2 shows a profile of mole fraction of 3,5-bis-(trifluoromethyl)-phenylboronic acid catalyst in the organic phase (toluene) versus pH. Circles represent modelled data, diamonds represent experimental data.

EXAMPLES

Example 1

Reaction Sequence (Absence of Catalyst)

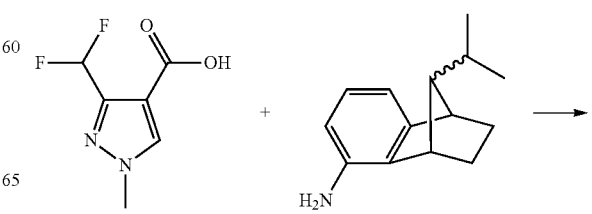

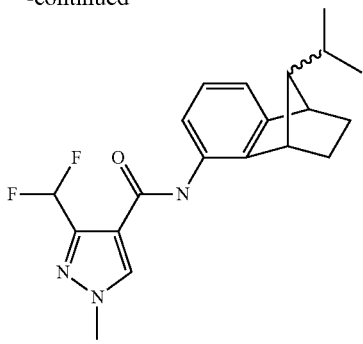

An oven-dried round bottomed flask was evacuated and refilled with nitrogen three times. The flask was fitted with a dropping funnel containing charged 3 Å molecular sieves, and this was connected to the nitrogen line. 3-Difluoromethyl-1-methyl-1H-pyrazole-4-carboxylic acid (0.36 g, 2 mmol), 9-Isopropyl-1,2,3,4-tetrahydro-1,4-methano-naphthalen-5-ylamine (0.4 g, 2 mmol) were added to the flask, followed by anhydrous toluene (2 mL) via syringe. The mixture was azeotropically refluxed overnight, under nitrogen. After this time, the solution was cooled and concentrated in vacuo to give a pale brown solid. $^1$H and $^{19}$F NMR and GC analyses showed only 5% conversion to amide product.

Example 2

Reaction Sequence

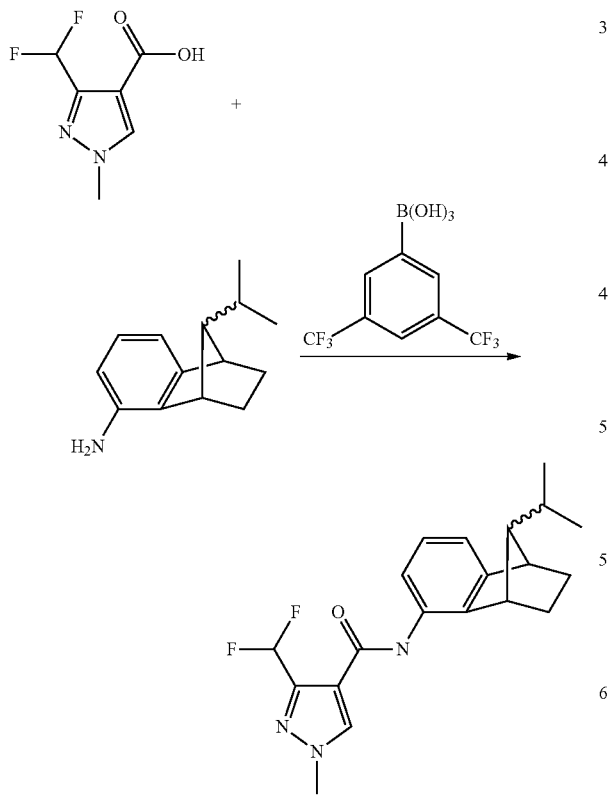

An oven-dried flask was evacuated and refilled with nitrogen three times. The flask was fitted with a dropping funnel containing charged 3 Å molecular sieves. 3-Difluoromethyl-1-methyl-1H-pyrazole-4-carboxylic acid (0.36 g, 2 mmol), 9-Isopropyl-1,2,3,4-tetrahydro-1,4-methano-naphthalen-5-ylamine (0.4 g, 2 mmol) were added to the flask, followed by 3,5-bis-(trifluoromethyl)-phenylboronic acid (26 mg, 5 mol %) and anhydrous toluene (4 mL). The mixture was heated to reflux and was azeotropically refluxed overnight under nitrogen. A sample was analysed by GC which indicated quantitative conversion to the amide and so the solution was cooled, and quenched with saturated aqueous solutions of sodium hydrogencarbonate (10 mL) and ammonium chloride (10 mL).

The aqueous layer was extracted with ethyl acetate (3×10 mL). Combined organic extracts were washed with water (10 mL), dried with MgSO$_4$ and concentrated in vacuo to give a brown solid which was identified as the amide product by $^1$H and $^{19}$F NMR, and GC-MS (0.55 g, 76%).

The boronic acid catalysed reaction was profiled using 10 mole % catalyst, under azeotropic reflux in toluene. The removal of water by azeotropic reflux appears to be advantageous, since without these conditions, reactions were not complete after 18 hours. See FIG. 1.

Recycling of the catalyst was by extracting the boronic acid from the reaction mass with strong aqueous alkali, acidifying and then re-extracting into toluene ready for the next batch was investigated. The phase partition was modelled using the calculated LogP (3.013) and pK$_a$ (6.57) and the experimental values are close although show a slight tail at the higher pH possibly due to the high ionic strength. See FIG. 2.

Catalyst recycle would significantly reduce the cost contribution of catalyst to the product.

Example 3

Reaction Sequence

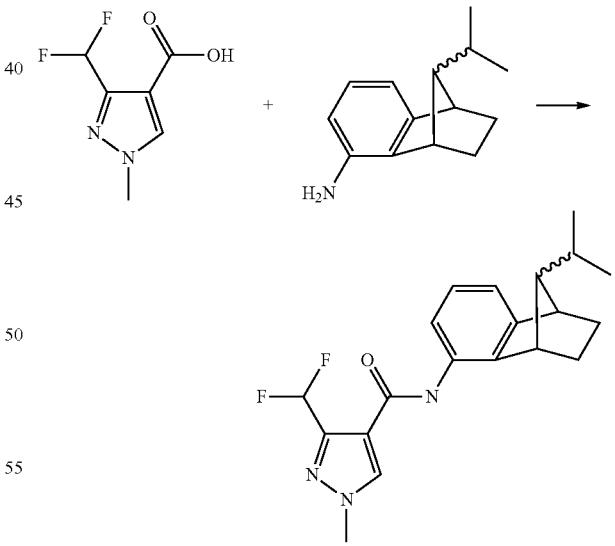

An oven-dried flask was evacuated and refilled with nitrogen three times. The flask was fitted with a dropping funnel containing charged 3 Å molecular sieves. 3-Difluoromethyl-1-methyl-1H-pyrazole-4-carboxylic acid (0.36 g, 2 mmol), 9-Isopropyl-1,2,3,4-tetrahydro-1,4-methano-naphthalen-5-ylamine (0.4 g, 2 mmol) were added to the flask, followed by antimony (III) ethoxide (34 µL, 5 mol %) and anhydrous toluene (4 mL). The reaction was refluxed azeotropically overnight, under an atmosphere of nitrogen. A sample was analysed by GC which indicated quantitative conversion to the amide and so the solution was quenched with methanol (5 mL), and a solid crashed out of the resulting solution. This suspension was filtered through a pad of Celite, washing with 50/50 ethyl acetate/acetone (10 mL). The resulting solution was concentrated in vacuo to yield a yellow solid which was identified by $^1$H and $^{19}$F NMR, and GCMS analyses as the amide product (0.53 g, 73%).

Example 4

Reaction Sequence

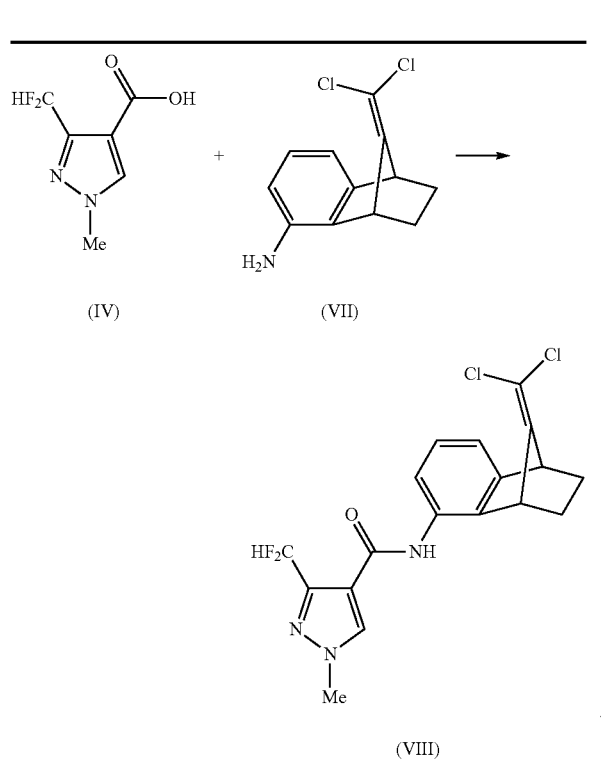

| Materials | Actual Wt (g) | Strength (%) | 100% Wt. (g) | Mol Wt. | mmol. | Mol. Ratio |
|---|---|---|---|---|---|---|
| DF-Pyrazole acid (IV) | 0.41 | 95.9 | 0.393 | 176 | 2.2 | 1.0 |
| Aniline (VII) | 0.52 | 95 | 0.494 | 239 | 2.2 | 1.0 |
| Boric acid | 0.0142 | 98 | 0.0139 | 61.8 | 0.23 | 0.1 |
| Xylene | 15 ml | 99 | — | — | — | — |

A 50 ml three neck round bottom flask was fitted with a magnetic flea, thermometer, oil bath, condenser, and Dean & Stark apparatus filled with 3 A molecular sieves 8-12 mesh (with 10 ml xylene). The system was purged with nitrogen and vented to atmosphere.

DF-Pyrazole acid (compound IV) (0.41 g), aniline (compound VII) (0.56 g), xylene (15 ml) and boric acid catalyst (14.2 mg) were charged to the flask. The mixture was heated to reflux (~144 deg C.) and held on temperature for 8 hrs. Reaction was monitored via GCMS.

Conversion = 94% conversion based on compound (IV) by GCMS

= 54% conversion based on compound (VIII) by GCMS

= 55% conversion by NMR

GC/MS Details: The product had the same retention time, molecular ion (M$^+$ 331) and fragmentation pattern as found with the authentic compound.

NMR: NMR spectrum of product was consistent with that for authentic material.

Example 5

Reaction Sequence

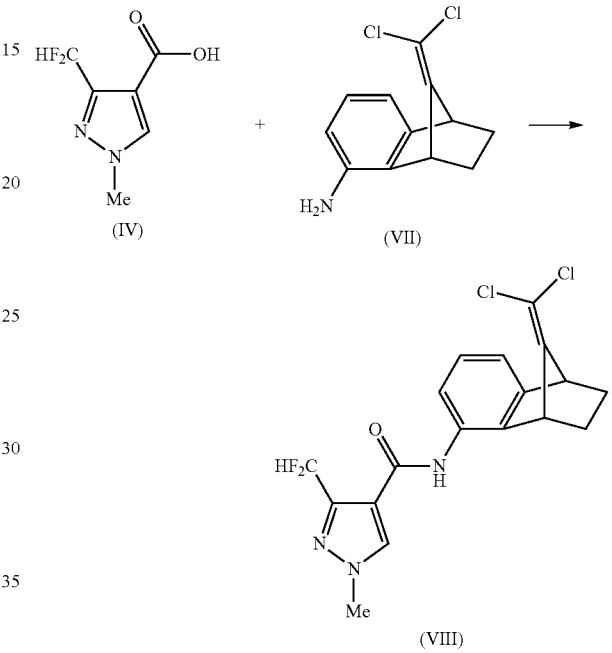

A selection of catalysts (10 mol %) were screened. The procedure in Example 4 was repeated varying the catalyst employed.

| Catalyst | Solvent | Conditions | Results |
|---|---|---|---|
| None | Xylene | Vigorous reflux with Dean & Stark set-up 5 hr | 2% conversion to desired product Relatively clean reaction |
| B(OH)$_3$ | Xylene | Vigorous reflux with Dean & Stark set-up 8 hr | 55% conversion to desired product Relatively clean reaction |
| (dimethylaminomethyl phenyl boronic acid structure) | Xylene | Vigorous reflux with Dean & Stark set-up. 8 hr | 55% conversion to the desired product |

Conversions were determined by GCMS analysis. The results presented in the table are based on consumption of the aniline component. Conversions based on carboxylic acid consumption are different, presumably due to response factor differences. NMR analysis has shown that monitoring aniline consumption gives the best measure of reaction conversion.

Desired product was formed in all cases, but reaction rate was very slow without catalyst present. Reasonably good rates were achieved with both of the boron-based catalysts tried. Interestingly, a synthetically advantageous rate was achieved with cheap boric acid catalyst (55% conversion in 8 hr), The product was isolated and its structure confirmed by NMR analysis.

Example 6

Reaction Sequence

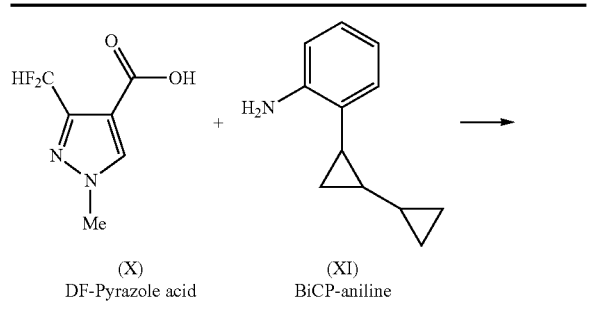

(X) DF-Pyrazole acid (XI) BiCP-aniline (IX) SYN 524,464

| Materials | Actual Weight | Strength % | 100% Weight | Molecular weight | Mmol | Molar Ratio |
|---|---|---|---|---|---|---|
| DF-Pyrazole acid (X) | 0.5 | 93.0 | 0.465 | 176 | 2.6 | 1.0 |
| BiCP Aniline (XI) | 0.94 | 48.7 | 0.458 | 173 | 2.6 | 1.0 |
| 2-(N,N-dimethyl-aminomethyl) phenylboronic acid | 0.047 | 98 | 0.046 | 179 | 0.26 | 0.1 |
| Xylene | 20 ml | 99 | 17.2 | 106 | 162 | 62.4 |

A 50 ml three neck round bottom flask was fitted with a magnetic flea, thermometer, oil bath, condenser, and Dean & Stark apparatus filled with 3 Å molecular sieves 8-12 mesh (with 10 ml xylene). The system was purged with nitrogen and vented to the atmosphere.

DF-pyrazole acid X (0.5 g), BiCP-aniline XI (0.94 g), xylene (20 ml) and 2-(N,N-dimethyl aminomethyl)phenylboronic acid catalyst (47 mg) were charged to the flask. The mixture was heated to reflux (~143° C.) and held at this temperature for 10 hours. The reaction was monitored via HPLC; 45% conversion being achieved after 5 hours, and 58% after 10 hours.

Product identity was confirmed by HPLC and GCMS comparison with authentic material.

Example 7

Reaction Sequence

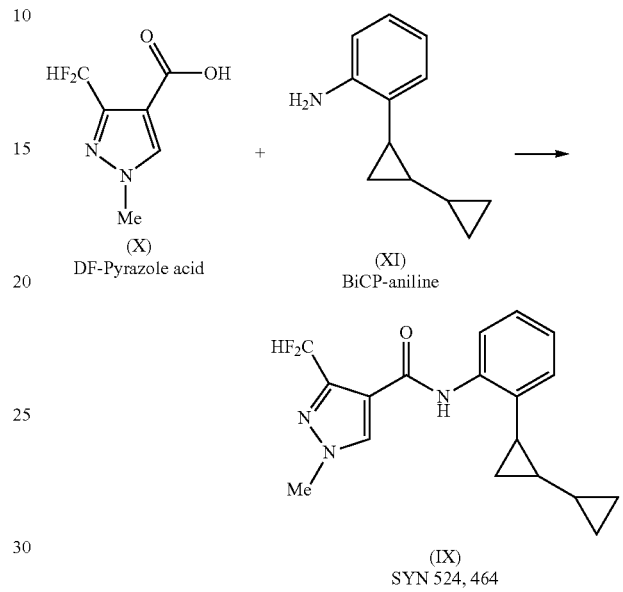

(X) DF-Pyrazole acid (XI) BiCP-aniline (IX) SYN 524, 464

The procedure of Example 6 was repeated varying the catalyst employed.

| Solvent | Conditions | Time | Catalyst | Conversion |
|---|---|---|---|---|
| Xylene | Reflux, Dean and Stark | 5 hours | None | <1% |
| Xylene | Reflux, Dean and Stark | 5 hours | 2-(N,N-dimethylaminomethyl) phenylboronic acid (10 Mol %) | 45% |
| Xylene | Reflux, Dean and Stark | 5 hours | Boric Acid (10 Mol %) | 25% |
| Xylene | Reflux, Dean and Stark | 20 hours | Boric Acid (10 Mol %) | 50% |

These results show that in the absence of catalysts, virtually no reaction occurred after 5 hours at 140° C.

Addition of catalyst, however, had a dramatic effect on reaction rate –45% conversion being achieved after 5 hours with 10% of 2-(N,N-dimethylaminomethyl) phenylboronic acid. Boric acid catalyst was less effective, but still generated a useful reaction rate (25% conversion after 5 hours).Product identity was confirmed by GCMS comparison with authentic material.

The invention claimed is:

1. A process for the preparation of compounds of the formula (I)

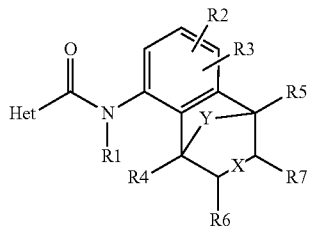

wherein
where Het is a 5- or 6-membered heterocyclic ring containing one to three heteroatoms, each independently selected from oxygen, nitrogen and sulphur, provided that the ring is not 1,2,3-triazole, the ring being substituted by groups R8, R9 and R10; X is a single or double bond; Y is O, S, N(R11) or (CR12R13)(CR14R15)m (CR16R17)n; m is 0 or 1; n is 0 or 1;

R1 is hydrogen, C1-4 alkyl, C1-4 haloalkyl, C1-4 alkoxy, C1-4 haloalkoxy, $CH_2C\equiv CR18$, $CH_2CR19=CHR20$, $CH=C=CH_2$ or COR21;

R2 and R3 are each, independently, hydrogen, halogen, C1-4 alkyl, C1-4 alkoxy or C1-4 haloalkoxy;

R4, R5, R6 and R7 are each, independently, hydrogen, halogen, C1-4 alkyl, C1-4 haloalkyl, C1-4 alkoxy, C1-4 haloalkoxy, C1-4 alkylthio, C1-4haloalkylthio, hydroxymethyl, C1-4 alkoxymethyl, $C(O)CH_3$ or $C(O)OCH_3$;

R8, R9 and R10 are each, independently, hydrogen, halogen, cyano, nitro, C1-4 alkyl, C1-4 haloalkyl, C1-4 alkoxy(C1-4)alkylene or C1-4 haloalkoxy(C1-4)alkylene, provided that at least one of R8, R9 and R10 is not hydrogen;

R11 is hydrogen, C1-4 alkyl, benzyl (in which the phenyl group is optionally substituted with up to three substituents, each independently selected from halogen, C1-4 alkyl, C1-4 haloalkyl and C1-4 alkoxy), formyl, C(O) C1-4 alkyl (optionally substituted by halogen or C1-4 alkoxy), C(=O)O—C1-6 alkyl (optionally substituted by halogen, C1-4 alkoxy or cyano) or C1-4 alkoxy (C1-4) alkylene;

R12, R13, R14, R15, R16 and R17 are each, independently, hydrogen, halogen, hydroxy, C1-6 alkyl, C2-6 alkenyl [both optionally substituted by halogen, hydroxy, C1-4 alkoxy, =O, aryl or O—C(O)—C1-4 alkyl or a 3-7 membered carboxylic ring (itself optionally substituted by up to three methyl groups)], a 3-7 membered saturated ring (optionally substituted by up to three methyl groups and optionally containing one heteroatom selected from nitrogen and oxygen) or C1-4 alkoxy; or R12 and R13 together with the carbon atom to which they are attached form the group C=O or a 3-5 membered carbocyclic ring (optionally substituted by up to three methyl groups and optionally with up to 2 heteroatoms each independently selected from O and N); or R12 and R13 together form a C1-6 alkylidene (optionally substituted by up to three methyl groups) or a C3-6 cycloalkylidene group (optionally substituted by up to three methyl groups);

R18, R19 and R20 are each, independently, hydrogen, halogen, C1-4 alkyl, C1-4 haloalkyl or C1-4 alkoxy(C1-4)alkylene; and R21 is hydrogen, C1-6 alkyl, C1-6 haloalkyl, C1-4 alkoxy (C1-4) alkylene, C1-4 alkyl-S—(C1-4) alkylene, C1-4 alkoxy or aryl;

comprising the step of reacting a carboxylic acid of formula (II)

wherein Het is as defined above
with an aniline of the formula (III)

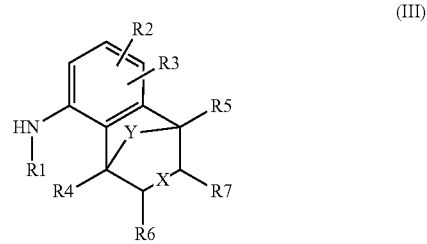

wherein R1, R2, R3, R4, R5, R6, R7, X and Y are as defined above;
in the presence of a boronic acid catalyst.

2. The process according to claim 1 wherein the boronic acid catalyst is boric acid.

3. The process according to claim 1 wherein the boronic acid catalyst is an aryl boronic acid.

4. The process according to claim 3 wherein the boronic acid catalyst is 2-(N,N-dimethylaminomethyl)phenylboronic acid.

5. The process according to claim 1 wherein the catalyst is employed in an amount of between 1 and 15 mol % based on the amount of carboxylic acid (II).

6. The process according to any claim 1 wherein the catalyst is employed in an amount of between 1 and 15 mol % based on the amount of aniline (III).

7. The process according to claim 1 wherein the molar ratio of acid (II): aniline (III) is in the range of from 2:1 to 1:2.

8. The process according to claim 1 wherein Het is pyrrolyl, pyrazolyl, thiazolyl, oxazolyl, pyridinyl, pyrimidyl, pyridazinyl, 2,3-dihydro-[1,4]oxathiine-6-yl, oxazinyl, thiazinyl or triazinyl.

9. The process according to claim 1 wherein Y is O, N(R11) or (CR12R13)(CR14R15)m(CR16R17)n.

10. The process according to claim 1 where R1 is hydrogen, $CH_2C \equiv CR18$, $CH=C=CH_2$ or COR21.

11. The process according to claim 1 wherein R2 is hydrogen, halogen or C1-4 alkyl.

12. The process according to claim 1 wherein R3 is hydrogen or methyl.

13. A process according to claim 1 for the preparation of a compound of formula (VI)

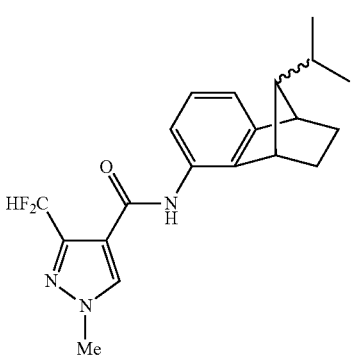
(VI)

comprising reacting a carboxylic acid of formula (IV)

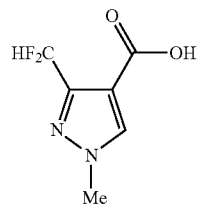
(IV)

with an aniline of formula (XI)

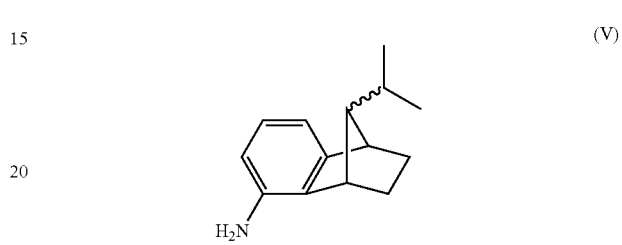
(V)

in the presence of a boronic acid catalyst.

* * * * *